United States Patent [19]

Starch

[11] Patent Number: 4,563,347
[45] Date of Patent: Jan. 7, 1986

[54] COMPOSITIONS USED TO CONDITION HAIR

[75] Inventor: Michael S. Starch, Midland, Mich.

[73] Assignee: Dow Corning Corporation, Midland, Mich.

[21] Appl. No.: 595,224

[22] Filed: Mar. 30, 1984

Related U.S. Application Data

[63] Continuation of Ser. No. 380,178, May 20, 1982, abandoned, and Ser. No. 453,855, Dec. 27, 1982, abandoned.

[51] Int. Cl.$^4$ .................. A45D 19/00; A61K 7/06
[52] U.S. Cl. ............................................. 424/70; 132/7
[58] Field of Search ................... 424/70, 184; 132/7

[56] References Cited

U.S. PATENT DOCUMENTS

| | | | |
|---|---|---|---|
| 3,956,174 | 5/1976 | Palcher | 252/400 R |
| 4,052,331 | 10/1977 | Dumoulin | 424/184 |
| 4,243,657 | 1/1981 | Okumura et al. | 424/47 |
| 4,247,592 | 1/1981 | Kalinowski | 428/266 |
| 4,311,695 | 1/1982 | Starch | 424/184 |
| 4,342,742 | 8/1982 | Sebag | 424/184 |

FOREIGN PATENT DOCUMENTS

| | | | |
|---|---|---|---|
| 2912484 | 10/1980 | Fed. Rep. of Germany | 424/70 |
| 2912485 | 10/1980 | Fed. Rep. of Germany | 424/70 |
| 0066638 | 6/1977 | Japan | 424/70 |
| 0066639 | 6/1977 | Japan | 424/70 |
| 66506 | 5/1980 | Japan | 424/70 |
| 136214 | 10/1980 | Japan | 424/70 |
| 187896 | 2/1964 | Switzerland | 424/184 |
| 535579 | 5/1973 | Switzerland | 424/70 |
| 802467 | 10/1958 | United Kingdom | 424/184 |
| 1206790 | 9/1970 | United Kingdom | 424/184 |
| 2058103 | 4/1981 | United Kingdom | 424/70 |
| 2084621 | 4/1982 | United Kingdom | 132/7 |

OTHER PUBLICATIONS

Todd et al., Amer. Perf. & Cosmetics, 10/1971.

*Primary Examiner*—Dale R. Ore
*Attorney, Agent, or Firm*—James E. Bittell

[57] ABSTRACT

A composition consisting essentially of a siloxane having substituents that provide attachment to the hair, surfactants, additives that provide freeze-thaw stability, and water is disclosed. The composition may also contain thickeners, and additives that reduce static electricity build-up, and fly-away. A method of conditioning hair which comprises applying to the hair the composition as defined above is also disclosed.

6 Claims, No Drawings

COMPOSITIONS USED TO CONDITION HAIR

This application is a continuation of application Ser. No. 380,178, filed May 20, 1982 and a continuation of application Ser. No. 453,855, filed Dec. 27, 1982, both now adandoned.

FIELD OF THE INVENTION

This invention relates to a composition that consists essentially of a siloxane having substituents that provide attachment to the hair, surfactants, freeze-thaw stability additives, and water. The composition may also contain thickeners and additives that reduce static electricity build-up, and fly-away. This invention further relates to a method of conditioning hair which comprises applying to the hair the above-defined composition.

DESCRIPTION OF THE PRIOR ART

It is well known that hair is easily damaged mechanically by combing, brushing, and washing. It is also known that hair is easily damaged physically and chemically by the sun, hair dryers, and permanents or other chemical treatments.

In most detergent compositions now in use, the removal of natural oils is unavoidable as a part of the cleansing action, and some hair is damaged as a result of the action of the detergent. Furthermore, shampoo compositions which thoroughly clean the hair usually leave it difficult to comb so that combing the hair produces an undesirable buildup of static electrical charges. In either case, the hair is very difficult to manage.

To overcome these problems, various alternative and complementary shampoo and hair conditioning systems have been explored. For example, many conventional shampoo compositions contain animal oils such as lanolin and beef tallow, glycols, fatty esters, or proteins in an effort to condition the hair by replacing stripped oils so as to leave the hair more manageable and natural after shampooing. However, when these derivatives are incorporated directly into a shampoo, they may cause a loss of sudsing and sheen, and leave the hair with a sticky and unnatural feel. Vegetable oils such as camellia oil and olive oil, mineral oils such as vaseline and paraffin, and synthetic oils have also been used either directly, as emulsions, or dissolved in solvents.

It is well known in the art that organopolysiloxanes give hair glossiness, suppleness, smoothness and softness. U.S. Pat. No. 4,243,657 discloses a hair dressing composed of dimethylpolysilxane and diol derivatives or a branched aliphatic alcohol. The use of dimethylpolysiloxanes, however, allows dust to easily adhere to the hair due to the oil build-up caused by the quantity of siloxane required. Hair conditioners composed of a polyorganosiloxane-polyoxyalkylene block copolymer and ethanol, such as those disclosed in Japanese Patent Sho 56[1980]-136214, have the problem in that they are easily removed when exposed to water. Great Britain Pat. No. 2,058,103 discloses hair grooming agents composed of (alkylamino) methylpolysiloxane and a cationic surfactant with an aqueous carrier. Though the siloxane is durable, it is not effective in dissipating static charges generated by combing. Moreover the level of durability achieved by this agent is not always desirable. Furthermore, its hydroxyl endblocking is believed to be the cause of some stability problems. Cationic modified organopolysiloxanes containing quaternary nitrogen is disclosed in Japanese Patent Sho 55[1980]-66506. These conditioners, however, are lacking in providing the hair suppleness, smoothness, and softness.

It is thus an object of this invention to provide a composition that is stable, somewhat durable, and imparts improved gloss, ease of combing, reduced fly-away, suppleness, smoothness, and softness to the hair. It is a further object of this invention to provide a method of conditioning hair, particularly hair that has been damaged by excessive shampooing or chemical treatments.

DETAILED DESCRIPTION

This invention relates to a composition that consists essentially of a siloxane having substituents that provide attachment to the hair, surfactants, freeze-thaw stability additives, and water. This composition may also contain thickeners and additives that reduce static electricity build-up and fly-away. This invention further relates to a method of conditioning hair which comprises applying to the hair the above defined composition.

Specifically, this invention relates to a composition consisting essentially of (A) a siloxane having the general formula

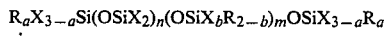

wherein

R is a functional group that provides attachment to the hair;

X is selected from the group consisting of hydrogen, phenyl, hydroxyl, and saturated hydrocarbon radicals composed of 1 to 8 carbon atoms;

a has a value of 0 to 3;

b has a value of 0 to 1; and n+m has a value of 1 to 2000 with n having a value of 0 to 1999 and m having a value of 1 to 2000;

(B) a surfactant;

(C) an additive that provides freeze-thaw stability; and (D) water.

The functional group on the siloxane, R, can be any group that provides attachment to the hair. It is preferred, however, that R be a monovalent radical having the general formula $C_yH_{2y}Z$ wherein y has a value of 2 to 8 and Z is selected from the group consisting of —NR'CH$_2$CH$_2$NR'$_2$, —COOH, —SCH$_2$COOH,

—NR'$_2$, —N$^+$R'$_3$A$^-$, —N$^+$R'H$_2$A$^-$, and —NR'CH$_2$CH$_2$N$^+$R'H$_2$A$^-$ wherein R' is selected from the group consisting of hydrogen, phenyl, benzyl, and monovalent saturated hydrocarbon radicals composed of 1 to 20 carbon atoms and A$^-$ is a halogen. Specific examples of monovalent saturated hydrocarbon radicals composed of 1 to 20 carbon atoms include methyl, ethyl, propyl, butyl, pentyl, hexyl, heptyl, octyl, nonyl, decyl, undecyl, dodecyl, tetradecyl, hexadecyl, octadecyl, and eicosyl radicals. Specific examples of suitable halides, A—, includes chlorides, bromides, iodides, and fluorides. It is optimal, however, that R be selected from the group consisting of C$_4$H$_8$NHCH$_2$CH$_2$NH$_2$, C$_4$H$_8$NHCH$_2$CH$_2$N$^+$R'H$_2$A$^-$ and C$_4$H$_8$COOH wherein R' is benzyl.

The substituent on the siloxane, denoted by X, is selected from the group consisting of hydrogen, phenyl, hydroxyl and saturated hydrocarbon radicals composed of 1 to 8 carbon atoms. Specific examples of suitable saturated hydrocarbon radicals includes methyl, ethyl, propyl, butyl, pentyl, hexyl, heptyl and octyl. It is preferred, however, that X be a methyl radical.

It is further preferred that a have a value of 0, b have a value of 1, and n+m have a value of 50 to 150 with n having a value of 49 to 149 and m having a value of 1 to 10.

The composition also contains (B) a surfactant, (C) an additive that provides freeze-thaw stability, and (D) water.

Though the type of surfactant employed is not critical for the purpose of this invention, typical surfactants include cationic, non-ionic, anionic, and mixtures thereof. The purpose of the surfactants are to maintain a stable dispersion of the silicone. Anionic surfactants include carboxylates, sulfonates, sulfates, and phosphate esters. Cationic surfactants include amines and quaternary salts. Non-ionic surfactants include polyoxyethylene derivatives of fatty alcohols, carboxylic esters, and carboxylic amides.

It is preferred that the surfactant be non-ionic. Specific examples of suitable non-ionic surfactants include polyoxyethylene octyl phenol containing 10 polyoxyethylene units, an alkyl ether of polyoxyethylene, an alkyl aryl ether of polyoxyethylene, trimethylnonyl polyethylene glycol ether, octyl phenoxy polyethoxy ethanol, and mixtures thereof. It is preferred that the surfactant be a mixture of approximately equal parts of trimethylnonyl polyethylene glycol ether and octyl phenoxy polyethoxy ethanol.

It is preferred that Component (C), the additive that provides freeze-thaw stability, be selected from the group consisting of ethylene glycol and glycerol. It is further preferred that it be ethylene glycol.

It is preferred that the composition to condition hair consist essentially of

| .1 to 61 | percent by weight Component (A), |
| .02 to 11.6 | percent by weight Component (B), |
| .003 to 2 | percent by weight Component (C), |
| and .16 to 99.88 | percent by weight Component (D). |

If desired, the composition may further contain (E) a thickener, and (F) an additive that reduces static electricity build-up and fly-away.

It is preferred that the thickener be selected from the group consisting of methylcellulose and a neutralized polymer of acrylic acid crosslinked with a polyfunctional agent.

It is preferred that (F) the additive that reduces static electricity build-up and fly-away be a quaternary amine. It is further preferred that the quaternary amine additive have the general formula $A^-N^+R'_4$ wherein $R'$ is selected from the group consisting of hydrogen, phenyl, benzyl, and monovalent saturated hydrocarbon radicals composed of 1 to 20 carbon atoms and $A^-$ is a halogen. Specific examples of suitable monovalent saturated hydrocarbon radicals composed of 1 to 20 carbon atoms include methyl, ethyl, propyl, butyl, pentyl, hexyl, heptyl, octyl, nonyl, decyl, undecyl, dodecyl, tetradecyl, hexadecyl, octadecyl and eicosyl. Specific examples of suitable halides, $A^-$, include, chlorides, bromides, iodides, and fluorides. It is optimal that the quaternary amine additive be $C_{18}H_{37}N^+(CH_3)_3Cl^-$. The quaternary amine additive also functions, to a certain extent, as a thickener.

It is optimal that the composition contain components (A),(B),(C),(D),(E), and (F). The ease of application to the hair is improved by the presence of all six (6) ingredients due to the viscosity increase. For convenience purposes only, it is preferred that the composition to condition hair have a viscosity range of 1000 centipoise to 100,000 centipoise at 25° C. and a pH value range of 7 to 9.

It is optimal that the composition consist essentially of

| .1 to 15 | percent by weight Component (A), |
| .012 to 2.85 | percent by weight Component (B), |
| .003 to .43 | percent by weight Component (C), |
| 73.72 to 99.685 | percent by weight Component (D), |
| .1 to 3 | percent by weight Component (E), |
| and .1 to 5 | percent by weight Component (F). |

The components of the present invention are well known to those skilled in the art so the preparation of the individual components will not be repeated here. It is preferred that the composition of the present invention be used as a hair conditioner treatment after shampooing. Any suitable method of application may be employed, for example immersion or spraying.

In addition to the essential ingredients, the composition of this invention may include minor quantities of optional materials which are added for specific purposes. Such other ingredients include, but are not limited to, medicaments solvents, perfumes, sequestering agents, opacifiers, and antimicrobial preservatives, of which silicone is one, all of which are commonly used and are well known to be capable of use in hair care formulations.

The hair conditioning composition of this invention also has the property of reducing the amount of water retained in hair and thus reducing the time required to dry the hair after application of the conditioning composition.

The term "hair" as used in the present invention includes treated and untreated human hair, animal hair, and any type of fiber that needs gloss, ease of combing, and reduced fly-away. Treated hair includes hair that is chemically changed and/or damaged by permanents and dyes.

In order that those skilled in the art may better understand how the present invention can be practiced, the following examples are given by way of illustration and not by way of limitation. All parts and percents referred to herein are by weight, and all viscosities are measured at 25° C. unless otherwise noted. The formulations were tested at water dilutions of 30%, but under normal use conditions, the formulations would be used as is, with no water dilution.

EXAMPLE 1

The following formulations were tested as conditioners on dark European hair swatches and compared to unconditioned dark European hair swatches on the basis of feel and ease of wet and dry combing. The combing rating scale ranged from 1 to 5 with 1 being easy to comb, very little resistance, and 5 being impossible to get the comb through the hair.

Formulation 1 was prepared by heating 90 grams of water to approximately 90° C. and then dispersing 2.0 grams of methylcellulose and 0.5 grams of sodium chloride in the water using a medium-shear mixing device. Stirring was continued until the dispersion was about 65° C. Then there was added 1.5 grams of stearalkonium chloride and 1.0 grams of cetyl alcohol, and it was made sure both these ingredients were thoroughly dispersed. The mixture was allowed to cool to 40° C. with stirring in such a way that no foam was generated. Finally there was added 5.0 grams of a material prepared as follows: Mix 3.60 grams octyl phenoxy polyethoxy ethanol, specifically Triton X-405 manufactured by Rohm and Haas Company, and 12 grams of water. Slowly, add 35.00 grams of

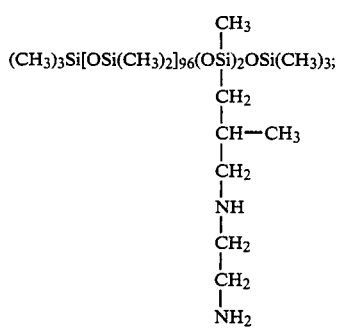

(This polymer normally contains 5% dimethylsiloxane cyclics as manufactured) with mixing. After stirring for 10 minutes, 3.06 grams of Tergitol TMN-6, a trimethylnonyl polyethylene glycol ether manufactured by Union Carbide Company, is added slowly. The mixture is then stirred for 3 hours using a high shear mixer. (Stirring for 1 hour and then passing through a colloid mill with a 0.015 inch gap is comparable). One gram of ethylene glycol and 45.34 grams of water is then added and the mixture is stirred until uniform.

Formulation 1 was then diluted to 30 percent in water for testing purposes.

Formulation 2 was prepared by dispersing and dissolving 0.24 grams Carbopol, a polymer of acrylic acid crosslinked with a polyfunctional agent manufactured by B.F. Goodrich Company, into 47.315 grams water and 0.13 grams sodium hydroxide into 47.315 grams water. Then the sodium hydroxide solution was added to the Carbopol solution while slowly stirring. Gellation is common as the sodium hydroxide solution is added. The pH of the mixture should be 7 or higher. If it is not, adjust upward with a small amount of sodium hydroxide. Next there was added 5.00 grams of a material prepared as follows: Mix 3.60 grams octyl phenoxy polyethoxy ethanol, specifically Triton X-405 manufactured by Rohm and Haas Company, and 12 grams of water. Slowly, add 35.00 grams of

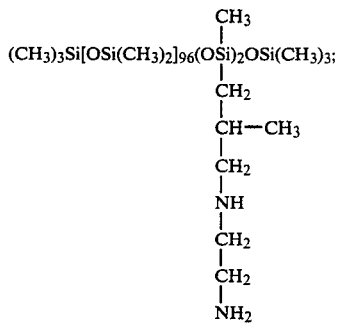

(This polymer normally contains 5% dimethylsiloxane cyclics as manufactured) with mixing. After stirring for 10 minutes, 3.06 grams of Tergitol TMN-6, a trimethylnonyl polyethylene glycol ether manufactured by Union Carbide Company, is added slowly. The mixture is then stirred for 3 hours using a high shear mixer. (Stirring for 1 hour and then passing through a colloid mill with a 0.015 inch gap is comparable). One gram of ethylene glycol and 45.34 grams of water is then added and the mixture is stirred until uniform.

Formulation 2 was then diluted to 30 percent in water for testing purposes.

The formulations were applied to wet hair, after it was shampooed, in an amount sufficient to thoroughly coat the hair. The conditioners were allowed to stay on the hair for 2 minutes and then were rinsed off with warm water. After evaluating the wet combing and wet feel, the hair was blown dry and then evaluated for dry combing.

The results are as follows:

| Test | Control | Formulation 1 | Formulation 2 |
| --- | --- | --- | --- |
| Wet Comb Rating | 3.5 | 1.2 | 1.0 |
| Wet Feel | Rough | Smooth | Smooth |
| Dry Comb Rating | 2.0 | 1.0 | 1.0 |

That which is claimed is:

1. A hair conditioning composition which is a stable dispersion of silicone and is formed by dispersing with shear a siloxane polymer into an aqueous phase, the composition consisting essentially of 0.1 to 61 percent by weight of (A) a siloxane having the general formula $R_aX_{3-a}Si(OSiX_2)_n(OSiX_bR_{2-b})_mOSiX_{3-a}R_a$ wherein R is a monovalent radical having the general formula $-C_yH_{2y}Z$ wherein y has a value of 2 to 8 and Z is selected from the group consisting of $-NR'CH_2CH_2NR'_2$, $-COOH$, $-SCH_2COOH$,

$-CNR'_2$, $-NR'_2$, $-N^+R'_3A^-$, $-N^+R'H_2A^{31}$, and $-NR'CH_2CH_2N^+R'H_2A^-$, wherein R; is selected from the group consisting of hydrogen, phenyl, benzyl, and monovalent saturated hydrocarbon radicals composed of 1 to 20 carbon atoms and $A^-$ is a halogen; X is selected from the group consisting of hydrogen, phenyl, hydroxyl, and saturated hydrocarbon radicals composed of 1 to 8 carbon atoms; a has a value of 0 to 3; b has a value of 0 to 1; and n+m has a value of 1 to 2000 with n having a value of 0 to 1999 and m having a value of 1 to 2000;

0.02 to 11.6 percent by weight of
(B) a surfactant selected from the group consisting of cationic, nonionic, and anionic surfactants;

0.003 to 2 percent by weight of
(C) a water soluble polyhydroxy alcohol; and 0.16 to 99.88 percent by weight of
(D) water.

2. The composition as defined in claim 1 wherein
X is methyl; a is 0; b is 1; and n+m has a value of 50 to 150 with n having a value of 49 to 149 and m having a value of 1 to 10;
(B) is a nonionic surfactant; and
(C) is a water soluble polyhydroxy alcohol.

3. The composition as defined in claim 2 wherein
(A) is the siloxane having the general formula $R_aX_{3-a}Si(OSiX_2)_n(OSiX_bR_{2-b})_mOSIX_{3-a}R_a$ wherein R is selected from the group consisting of $C_4H_8NHCH_2CH_2NH_2$, $C_4H_8NHCH_2CH_2N^+R'H_2A^-$ and $C_4H_8COOH$ wherein R' is benzyl;
(B) is a mixture of approximately equal parts of trimethylnonyl polyethylene glycol ether and octyl phenoxy polyethoxy ethanol; and
(C) is selected from the group consisting of ethylene glycol and glycerol.

4. A method for conditioning hair which comprises applying to the hair the composition as defined in claim 1.

5. A method for conditioning hair which comprises applying to the hair the composition as defined in claim 2.

6. A method for conditioning hair which comprises applying to the hair the composition as defined in claim 3.

* * * * *

UNITED STATES PATENT AND TRADEMARK OFFICE
CERTIFICATE OF CORRECTION

PATENT NO. : 4,563,347

DATED : January 7, 1986

INVENTOR(S) : Michael S. Starch

It is certified that error appears in the above-identified patent and that said Letters Patent is hereby corrected as shown below:

1. In column 6, line 61, "$-N^+R'H_2A^{31}$," should read -- $-N^+R'H_2A^-$, --.

Signed and Sealed this

Second Day of September 1986

[SEAL]

Attest:

DONALD J. QUIGG

Attesting Officer

Commissioner of Patents and Trademarks